United States Patent [19]

Dwyer et al.

[11] 4,091,007
[45] May 23, 1978

[54] PREPARATION OF ZEOLITES

[75] Inventors: Francis G. Dwyer, West Chester; Albert B. Schwartz, Philadelphia, both of Pa.

[73] Assignee: Mobil Oil Corporation, New York, N.Y.

[21] Appl. No.: 627,158

[22] Filed: Oct. 30, 1975

Related U.S. Application Data

[63] Continuation-in-part of Ser. No. 311,190, Dec. 1, 1972, abandoned, which is a continuation-in-part of Ser. No. 886,401, Dec. 18, 1969, abandoned.

[51] Int. Cl.$^2$ .................... C01B 33/28; C07F 5/06
[52] U.S. Cl. .................... 260/448 C; 252/455 Z; 423/118
[58] Field of Search ............... 423/118, 328, 329, 330; 252/455 Z; 260/448 C

[56] References Cited

U.S. PATENT DOCUMENTS

| 2,992,068 | 7/1961 | Haden et al. ............... 423/118 |
| 3,119,659 | 1/1964 | Taggart et al. ............. 423/118 |
| 3,119,660 | 1/1964 | Howell et al. .............. 423/118 |
| 3,431,218 | 3/1969 | Plank et al. ............... 423/118 X |
| 3,515,682 | 6/1970 | Flank et al. ............... 252/455 Z |
| 3,642,434 | 2/1972 | Dwyer ..................... 423/329 |
| 3,702,886 | 11/1972 | Argaver et al. ............ 423/328 |
| 3,849,463 | 11/1974 | Dwyer et al. .............. 423/328 X |

FOREIGN PATENT DOCUMENTS 1,117,568  6/1968  United Kingdom ............... 423/328

*Primary Examiner*—Edward J. Meros
*Attorney, Agent, or Firm*—Charles A. Huggett; Raymond W. Barclay; Dennis P. Santini

[57] ABSTRACT

An improved method for preparing a crystalline aluminosilicate zeolite having uniform pores and greater than 40 percent crystallinity which comprises forming a critical reaction mixture containing a source of at least two cations, silica, alumina and water, wherein at least about 70 weight percent of the alumina is provided to the reaction mixture by an alumina-containing clay being added thereto, and maintaining the reaction mixture at a temperature and pressure for a time necessary to crystallize the crystalline aluminosilicate from the reaction mixture. It is desirable to preform said reaction mixture into discrete particles such as pellets or extrudates which retain their shape and acquire substantial strength in the crystallization process.

18 Claims, No Drawings

PREPARATION OF ZEOLITES

CROSS-REFERENCE TO RELATED APPLICATIONS

This is a continuation-in-part of application Ser. No. 311,190, filed Dec. 1, 1972, now abandoned, which was a continuation-in-part of application Ser. No. 886,401, filed Dec. 18, 1969, now abandoned.

BACKGROUND OF THE INVENTION

1. Field of the Invention

This invention relates to an improved method for preparation of zeolites ZSM-4 and ZSM-5 which have uniform pores and which are greater than 40% crystalline. The improvement resides in forming a reaction mixture in each instance having a specific critical compositional range as follows:

|  | ZSM-4 | ZSM-5 |
|---|---|---|
| $Na_2O + R_2O/Al_2O_3$ | 0.60–1.75 | 0.15–0.85 |
| $Na_2O + R_2O/SiO_2$ | 0.24–0.65 | 0.04–0.18 |
| $Na_2O/Na_2O + R_2O$ | 0.75–0.92 | 0.30–0.85 |
| $SiO_2/Al_2O_3$ | 1.8–4.3 | 1.8–6.0 |
| $H_2O/R_2O + Na_2O$ | 9–60 | 35–360 | wherein R is a tetramethylammonium cation for ZSM-4 preparation and a tetraalkylammonium cation, the alkyl groups of which preferably contain 2–5 carbon atoms, for ZSM-5 preparation, and wherein at least about 70 weight percent of the $Al_2O_3$ is provided by an alumina-containing clay, e.g. kaolin, being added to the reaction mixture.

DISCUSSION OF THE PRIOR ART

Crystalline aluminosilicates have been prepared from mixtures of oxides including sodium oxide, alumina, silica and water. More recently clays and coprecipitated aluminosilicate gels, in the dehydrated form, have been used as sources of alumina and silica in reaction systems. In some instances of the synthetic faujasite synthesis from clay, the zeolitic product is in the form of an aggregate.

Recently, new synthetic aluminosilicate zeolites ZSM-4 and ZSM-5 have been discovered. ZSM-4 is described in Canadian patent 817,915 and ZSM-5 is described in U.S. Pat. No. 3,702,886. One of the distinguishing characteristics of these zeolites is that at least two cationic species are present in both the reaction mixture and the zeolitic product. Many catalytic applications of these zeolites lend themselves to using catalyst particles containing high crystalline aluminosilicate contents. It is desirable to synthesize these crystalline aluminosilicates in a hard aggregate form that readily permits subsequent chemical processing, such as ion exchange, and eliminates the need for reformulation and pelletizing prior to use as a catalyst or adsorbent. The methods of the prior art are not effective in obtaining highly crystalline zeolitic products (e.g. greater than 40% crystalline at the time of formation) in hard aggregate form for the systems containing at least two cationic species such as ZSM-4 and ZSM-5.

It is therefore an objective of the present invention to provide a method whereby polycationic crystalline aluminosilcates ZSM-4 and ZSM-5 can be synthesized in a hard aggregate form having crystallinity of greater than 40% at the time of formation.

SUMMARY OF THE INVENTION

An improved method for preparing a crystalline aluminosilicate zeolite, i.e. ZSM-4 or ZSM-5, is provided which comprises forming a critical reaction mixture containing a source of at least two cations, silica, alumina and water, wherein at least about 70 weight percent of the alumina is provided by an alumina-containing clay being added to the reaction mixture, and maintaining the reaction mixture at a temperature and pressure for a time necessary to crystallize the aluminosilicate from the reaction mixture.

DESCRIPTION OF SPECIFIC EMBODIMENTS

It is an objective of the present invention to prepare zeolitic crystalline aluminosilicates by crystallizing a reaction mixture which includes a clay as the major source of alumina, an added source of silica, water and an added source of at least two cations.

The generic title of clay is meant to include alumina-containing clays such as kaolinite, halloysite, montmorillonite, illite, dickite, attapulgite, and others. Although the zeolitic crystalline aluminosilicate can be prepared using either the raw clay or a thermally or hydrothermally treated clay, it is preferred that the clay be given a thermal treatment at a temperature of 1000° F or above. It is also understood that chemically treated clays may be utilized in this invention.

It is important in the present improved method that at least about 70 weight percent of the alumina component of the reaction mixtures be provided by the alumina-containing clay which is added to the reaction mixture. Up to 100 weight percent of the alumina component may be provided by the clay with benefits relative to cost realizable. It is preferred that at least about 80 weight percent of the reaction mixture alumina component be provided by an alumina-containing clay.

The source of silica in the reaction mixture may be both a clay and a non-clay added source of silica or a clay alone. Typical non-clay added sources of silica that can be employed in the synthesis are Ludox, an aqueous dispersion of colloidal silica, water glass, sand, silica gel, fumed silica and finely-divided precipitated silicas such as Hi-Sil, Quso, and Zeosyl 100.

The ratio of added silica from a non-clay source to clay in the reaction mixture of the present method may vary from 0 (where all silica in the reaction mixture is provided by the clay) to about 5 (where one or more of the above non-clay sources of silica is used in the reaction mixture). In general, when the reaction mixture is intended to provide ZSM-4, the ratio may be preferably from 0 to about 0.75. Also, when the reaction mixture is intended to provide ZSM-5, the ratio may be preferably from about 0.05 to about 1.

The cations added to the reaction mixture are selected on the basis of the zeolite that it is desired to crystallize and are, for example, represented by groups such as the alkali metals: $Na^+$, $K^+$, $Li^+$, $Cs^+$ and $Rb^+$; quaternary alkyl ammonium ions: $(CH_3)_4N^+$, $(C_2H_5)_4N^+$, $(C_3H_7)_4N^+$, $(C_4H_9)_4N^+$ and $(CH_3)_3(C_2H_6)N^+$; and other quarternary compounds such as quarternary alkyl aryl ammonium ions such as dimethyl diphenyl ammonium and still other quaternary ammonium ions such as trimethyl benzyl ammonium as well as quarternary phosphonium, arsenium and stilbonium ions.

The water content of the reaction mixture will depend on the final physical form the particles desired. It is preferred to have less than 50 weight percent water in the reaction mixture when preparing aggregates in the form of extrudates, tablets, spheroids, or granules. For each form of the aggregate, some adjustment in water content, below 50 weight percent, will be made to impart the best physical properties to the mixture. For example, less water is desired for tableting the mixture than extruding it. On the other hand, if the mixture is to be spray dried, enough water has to be added to prepare a fluid enough slurry to be pumped through the spraying nozzle.

For some catalytic or adsorption applications, it will be desirable to incorporate substantially nonreactive solid powders to the reaction mixture. The powders are selected on the basis of the particular physical property that it is desired to impart to the final product. For example, solid powders may be added to increase density, increase heat capacity or modify porosity of the final particle, or act as a diluent for the crystalline aluminosilicate in the product. Examples of solid powders which may be used include alpha alumina, titania, zirconia, zircon, barium sulfate, and nickel metal. It is to be understood that substantially inactive "weighing agents" such as inactive alumina (e.g. alpha alumina) and sand may also be used.

Principal objects of the present invention are to prepare zeolites known as ZSM-4 and ZSM-5 from reaction mixtures in which the alumina requirement for the ZSM-4 or ZSM-5 is supplied primarily from a clay or other inexpensive material.

ZSM-4 is a relatively new zeolite which, in its as synthesized aluminosilicate form, has the following composition in its anhydrous state, expressed in terms of mole ratios of oxides:

$$0.9 \pm 0.2\ M_{\frac{2}{n}}O: Al_2O_3: 3\text{--}20\ SiO_2$$

where M is a mixture of tetramethylammonium cations and alkali metal cations, especially sodium. Generally, the tetramethylammonium cations comprise between 1 and 50 percent of the cations in the as synthesized form. ZSM-4 has a distinctive X-ray diffraction pattern which further identifies it from other known zeolites. The original alkali metal cations of ZSM-4 can be exchanged by ion exchange with other ions to form species of the zeolite which have exceptional catalytic properties.

ZSM-4 is generally prepared by forming a mixture of alumina, silica, sodium oxide, water and tetramethylammonium compounds such that the mixture has a composition, in terms of mole ratios of oxides, falling within the following range:

| | |
|---|---|
| $\dfrac{\text{Alkali Metal Oxide}}{\text{Alkali Metal Oxide} + R_2O}$ | 0.31 to < 1 |
| $\dfrac{R_2O + \text{Alkali Metal Oxide}}{SiO_2}$ | .05 to .90 |
| $\dfrac{SiO_2}{Al_2O_3}$ | 3 to 60 |
| $\dfrac{H_2O}{R_2O + \text{Alkali Metal Oxide}}$ | 15 to 600 | wherein R is a tetramethylammonium cation. The mixture is maintained under conditions of temperature and pressure until crystals are formed which crystals are separated and recovered.

Members of the family of ZSM-4 zeolites possess a definite distinguishing crystalline structure whose X-ray diffraction pattern has the following values:

TABLE 1

| Interplanar Spacing d(A) | Relative Intensity |
|---|---|
| 9.1 ± .2 | vs |
| 7.94 ± .1 | mw |
| 6.90 ± .1 | m |
| 5.97 ± .07 | s |
| 5.50 ± .05 | mw |
| 5.27 ± .05 | mw |
| 4.71 ± .05 | mw |
| 4.39 ± .05 | w |
| 3.96 ± .05 | w |
| 3.80 ± .05 | s |
| 3.71 ± .05 | m |
| 3.63 ± .05 | m |
| 3.52 ± .05 | s |
| 3.44 ± .05 | m |
| 3.16 ± .05 | s |
| 3.09 ± .05 | m |
| 3.04 ± .05 | m |
| 2.98 ± .05 | m |
| 2.92 ± .05 | s |

These values were determined by standard techniques. The radiation was the K-alpha doublet of copper, and a Geiger counter spectrometer with a strip chart pen recorder was used. The peak heights, I, and the positions as a function of 2 times theta, where theta is the Bragg angle, were read from the spectrometer chart. From these, the relative intensities, $100\ I/I_o$, where $I_o$ is the intensity of the strongest line or peak, and d(obs.), the interplanar spacing in A, corresponding to the recorded lines, were calculated. In Table I, the relative intensities are given in terms of the symbols $vs$ = very strong, $w$ = weak, $s$ = strong, $m$ = medium, and $mw$ = medium weak. It should be understood that this X-ray diffraction pattern is characteristic of all the species of ZSM-4 compositions. Ion exchange of the sodium ion with another cation reveals substantially the same pattern with some minor shifts in interplanar spacing and variation in relative intensity.

It will be observed, therefore, that in preparation of ZSM-4 in addition to a source of sodium oxide, there must be present a source of tetramethylammonium cation as the zeolite is formed in a form which contains tetramethylammonium cations in the structure. Otherwise, the ratio of oxides is supplied by materials such as sodium silicate, colloidal silica, sodium hydroxide, tetramethylammonium hydroxide, tetramethylammonium chloride and water. The alumina requirement of this invention is supplied mainly by the clay which is added to the reaction mixture.

ZSM-5 compositions (in anhydrous state) can also be identified, in terms of mole ratios of oxides, as follows:

$$0.9 \pm 0.2\ M_{\frac{2}{n}}O : Al_2O_3: x\ SiO_2$$

wherein M is selected from the group consisting of a mixture of alkali metal cations, especially sodium, and tetraalkylammonium cations, the alkyl groups of which preferably contain 2–5 carbon atoms and $x$ is at least 5.

Members of the family of ZSM-5 zeolites possess a definite distinguishing crystalline structure whose X-ray diffraction pattern shows the following significant lines:

TABLE 2

| Interplanar Spacing d(A) | Relative Intensity |
|---|---|
| 11.1 ± 0.3 | s |

TABLE 2-continued

| Interplanar Spacing d(A) | Relative Intensity |
|---|---|
| 10.0 ± 0.3 | s |
| 7.4 ± 0.2 | w |
| 7.1 ± 0.2 | w |
| 6.3 ± 0.2 | w |
| 6.04 ± 0.2 | w |
| 5.97 ± 0.2 | w |
| 5.69 ± 0.1 | w |
| 5.56 ± 0.1 | w |
| 5.01 ± 0.1 | w |
| 4.60 ± 0.1 | w |
| 4.35 ± 0.1 | w |
| 4.25 ± 0.1 | w |
| 3.85 ± 0.1 | vs |
| 3.75 ± 0.05 | s |
| 3.71 ± 0.05 | s |
| 3.64 ± 0.05 | m |
| 3.04 ± 0.05 | w |
| 2.99 ± 0.05 | w |
| 2.94 ± 0.05 | w |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, $100 \ I/I_o$, where $I_o$ is the intensity of the strongest line or peak, and d(obs.), the interplanar spacing in A, corresponding to the recorded lines, were calculated. In Table 2, the relative intensities are given in terms of the symbols $s$ = strong, $m$ = medium, $w$ = weak and $vs$ = very strong.

Zeolite ZSM-5 can be suitably prepared by preparing a solution containing tetrapropylammonium hydroxide, sodium oxide, an oxide of aluminum, an oxide of silica, and water and having a composition falling within the following ranges:

TABLE 3

| | Broad | Preferred | Particularly Preferred |
|---|---|---|---|
| $OH^-/SiO_2$ | 0.07–10.0 | 0.1–0.8 | 0.2–0.75 |
| $R_4N^+/(R_4N^+ + Na^+)$ | 0.01–0.95 | 0.02–0.9 | 0.02–0.80 |
| $H_2O/OH^-$ | 10–300 | 10–300 | 10–300 |
| $SiO_2/Al_2O_3$ | ≧ 5 | 5–300 | 15–300 | wherein R is propyl, maintaining the mixture until crystals of the zeolite are formed. It is noted that an excess of tetrapropylammonium hydroxide can be used which would raise the value of $OH^-/Si_2O$ above the ranges set forth supra. The excess hydroxide, of course, does not participate in the reaction. Thereafter, the crystals are separated from the liquid and recovered. Typical reaction conditions consist of heating the foregoing reaction mixture to a temperature of from about 75° C to 205° C for a period of time of from about one hour to 60 days. A more preferred temperature range is from about 90° to 175° C with the amount of time at a temperature in such range being from about 1 hour to 20 days.

In order to achieve the improved zeolite product by way of the present method, i.e. a ZSM-4 or ZSM-5 having uniform pores and being greater than about 40% crystalline, the reaction mixture must be composed of $Al_2O_3$, $SiO_2$, $H_2O$, $Na_2O$ and $R_2O$, wherein R is as above defined and wherein at least about 70 weight percent of the $Al_2O_3$ is provided by an added alumina-containing clay as above defined, according to the following mole ratio ranges:

| | ZSM-4 | ZSM-5 |
|---|---|---|
| $Na_2O + R_2O/Al_2O_3$ | 0.60–1.75 | 0.15–0.85 |
| $Na_2O + R_2O/SiO_2$ | 0.24–0.65 | 0.04–0.18 |
| $Na_2O/Na_2O + R_2O$ | 0.75–0.92 | 0.30–0.85 |
| $SiO_2/Al_2O_3$ | 1.8–4.3 | 1.8–6.0 |
| $H_2O/R_2O + Na_2O$ | 9–60 | 35–360 |

It is desirable in the method of this invention to preform the clay containing reaction mixture into discrete particles such as pellets or extrudates. These particles retain their shape and acquire substantial strength in the crystallization process. The crystallized product now can be readily handled in any subsequent chemical processing, such as ion exchange, without necessitating such cumbersome processes as filtration. Furthermore, the discrete particles can be directly used as adsorbents or catalysts after the appropriate processing but without need of any reformulation or pelletizing.

Zeolites prepared by the improved method can be ion exchanged in accordance with known techniques to prepare catalytically-active forms. It has been found that synthetic faujasite prepared by the technique of the present invention can be exchanged into a form containing rare earth and hydrogen ions. When subjected to tests to determine the activity of the material for cracking hexane, it was found that it was more than 200 times more active than a standard silica-alumina cracking catalyst material.

Zeolites prepared pursuant to the present invention can be employed in the as synthesized form or can be converted into forms through ion exchange. Zeolites can be ion exchanged to remove at least a portion of the alkali metal cations and converted into forms which tend to be more catalytically active and stable. The alkali metal cations, especially the sodium and potassium cations, can be exchanged for hydrogen ions by treating the zeolite with acids. Alternatively, it can be treated with a source of ammonium, alkylammonium or arylammonium, providing steric hinderances do not prevent the cation from entering the cages of the zeolite. If the alkali metal is replaced by an ammonium cation or complex, the hydrogen form is prepared therefrom by heating the exchanged composition at a temperature above about 400° F causing evolution of ammonia and retention of a proton in the composition, at the site previously occupied by the ammonium ion.

Other replacing cations include cations of Groups IB-VIII of the Periodic Table, especially metals Groups II and III, including the rare earth metals, tin, lead, Group IVB comprising titanium, zirconium, and hafnium; metals of the actinide series, antimony, bismuth, chromium; also Group VIIB and Group VIII. Regardless of the cations replacing the alkali metal cations in the as synthesized form of the zeolites, the spatial arrangement of the aluminum, silicon and oxygen atoms, which form the basic crystal lattice of the zeolite, remains essentially unchanged by the described replacement of sodium as determined by X-ray diffraction analysis of the ion exchanged material.

Ion exchange of the zeolites prepared hereby can be accomplished conventionally by contacting the zeolite with a solution, suitably an aqueous solution, of a salt of the exchanging cation. Additionally, the composition can undergo solid state exchange to remove sodium and substitute another cation therefor. Preferably, a solution exchange is employed.

While water will ordinarily be the solvent in the base exchange solution employed, it is contemplated that other solvents, although generally less preferred, can be used. Thus, in addition to an aqueous solution, alcohol solutions and the like of the exchange compounds can be employed in producing a catalyst composition. Generally, the alkali metal content is reduced to less than 5 percent by weight and preferably less than 3 weight percent. When the exchanged aluminosilicate is prepared, it is generally, thereafter, treated with a suitable solvent, e.g. water, to wash out any of the anions which may have become temporarily entrained or caught in the pores or cavities of the crystalline composition.

In order to more fully illustrate the nature of the present invention and the manner of practicing the same, the following examples are presented:

EXAMPLE 1

Thirty grams of Georgia kaolin, calcined 5 hours at 1700° F in air, was blended dry with 150 grams of Georgia kaolin, calcined 6 hours at 1500° F in air, in a Waring blender. To this dry blend was added a solution prepared by dissolving 30 grams of NaOH (98.4% NaOH) in 115.6 grams of Ludox (LS) (colloidal dispersion of 30 wt. % $SiO_2$ and having an $SiO_2/Na_2O$ mole ratio of 285) then adding 30 grams of 24 percent by weight solution of tetramethylammonium hydroxide in methanol. The mixture was thoroughly blended and then allowed to age at room temperature overnight. The reaction mixture had the following composition in mole ratios of oxides:

$Na_2O + R_2O/Al_2O_3$; 0.52
$Na_2O + R_2O/SiO_2$; 0.23
$Na_2O/Na_2O + R_2O$; 0.90
$SiO_2/Al_2O_3$; 2.71
$H_2O/R_2O + Na_2O$; 11.7

After aging the mixture set up into a hard lump that was broken up into granules. The granules were placed in polypropylene jars and put into a steam chest, at 100° C, to crystallize. After 17 days the material was removed from the steam chest, washed free of excess alkali and dried.

X-ray diffraction analysis of the product zeolite of this example proved it to be devoid of any crystalline ZSM-4 or ZSM-5. It was composed primarily of zeolite A. This demonstrates the critical function of the reaction mixture composition in the present improved method.

EXAMPLE 2

One hundred eighty grams of Georgia kaolin in the raw state as recieved was added to a solution containing 361 grams of Q-brand sodium silicate (28.5 wt. % $SiO_2$, 8.8 wt. % $Na_2O$ and 62.7 wt. % $H_2O$), 45 grams of NaOH pellets (98.2 wt. % NaOH) and 69 grams of a 50 wt. % water solution of tetramethylammonium chloride. The mixture was then transferred to a polypropylene jar and put into a steam chest at 100° C to crystallize. The reaction mixture had the following composition in mole ratios of oxides:

$Na_2O + R_2O/Al_2O_3$; 1.78
$Na_2O + R_2O/SiO_2$; 0.40
$Na_2O/Na_2O + R_2O$; 0.88
$SiO_2/Al_2O_3$; 4.45
$H_2O/R_2O + Na_2O$; 11.8

After 8 days the mixture was removed from the steam chest, washed free of excess alkali and dried. X-ray diffraction analysis of the product of this example proved it to be composed of less than 20 weight percent crystalline ZSM-4. The remainder of the product was composed of various other amorphous and crystalline materials, including kaolinite and zeolite P. This example further demonstrates the critical function of the reaction mixture in the present improved method.

EXAMPLE 3

One hundred eighty grams of Georgia kaolin, calcined 6 hours at 1700° F was added to a solution containing 361 grams of Q-brand sodium silicate, 60 grams of NaOH (98.2% NaOH) and 69 grams of a 50 percent weight water solution of tetramethylammonium chloride. After thorough mixing on a Waring blender, the mixture was transferred to a polypropylene jar and placed into a steam chest at 100° C to crystallize. The reaction mixture had the following composition in mole ratios of oxides:

$Na_2O + R_2O/Al_2O_3$; 1.73
$Na_2O + R_2O/SiO_2$; 0.42
$Na_2O/Na_2O + R_2O$; 0.90
$SiO_2/Al_2O_3$; 4.11
$H_2O/R_2O + Na_2O$; 9.0

After 42 hours the material was removed from the steam chest and a portion was washed free of excess alkali and dried. X-ray diffraction analysis of the washed sample showed it to be composed of 80 weight percent crystalline ZSM-4.

EXAMPLE 4

One hundred eighty grams of Georgia kaolin in the raw, as received state was slowly added to a solution containing 361 grams of Q-brand sodium silicate, 30 grams of NaOH pellets (98.2% wt. NaOH) and 69 grams of a 50% weight water solution of tetramethylammonium chloride. The mixture was thoroughly blended by mixing in a Waring blender for about 5 minutes. The mixture was then transferred to a polypropylene jar and put into a steam chest at 100° C to crystallize. The reaction mixture had the following composition in mole ratios of oxides:

$Na_2O + R_2O/Al_2O_3$; 1.28
$Na_2O + R_2O/SiO_2$; 0.31
$Na_2O/Na_2O + R_2O$; 0.86
$SiO_2/Al_2O_3$; 4.11
$H_2O/R_2O + Na_2O$; 14.3

After 121½ hours, the mixture was removed from the steam chest, washed free of excess alkali and dried. X-ray diffraction analysis of the product showed it to be composed of 80 weight percent crystalline zeolite ZSM-4.

EXAMPLE 5

Fifteen grams of Georgia kaolin, calcined 6 hours at 1700° F in air and 75 grams of Georgia kaolin, calcined 6 hours at 1500° F in air, were thoroughly mixed. The clay mixture was then added to a solution containing 180.5 grams of Q-brand sodium silicate, 15 grams of NaOH pellets (98.1% wt. NaOH) and 30 grams of a 24% weight solution of tetramethylammonium hydroxide in methanol. The mixture was transferred to a polypropylene jar and aged at ambient temperature for approximately 90 hours. The mixture was then placed in a steam chest at 100° C to crystallize. The reaction mixture had the following composition in mole ratios of oxides:

$Na_2O + R_2O/Al_2O_3$; 1.19
$Na_2O + R_2O/SiO_2$; 0.29

$Na_2O/Na_2O+R_2O$; 0.93
$SiO_2/Al_2O_3$; 4.11
$H_2O/R_2O+Na_2O$; 13.0

After 7 days the mixture was sampled and the sample was washed free of excess alkali and dried. X-ray diffraction analysis revealed the product of this example to be composed of only a trace amount of crystalline ZSM-4, with the remainder thereof being various other amorphous and crystalline materials, including zeolite S. This example is a further demonstration of the critical function of the reaction mixture in the present method.

EXAMPLE 6

A solution containing 270.8 grams of Q-brand sodium silicate, 92 grams of NaOH pellets (98.3% wt. NaOH), 20 grams of NaCl and 60 grams of a 50 weight percent water solution of tetramethylammonium chloride was mixed with 600 grams of Georgia kaolin, calcined 6 hours at 1700° F in air. The mixture was thoroughly blended in a Muller mixer for 3 hours during which 80 cc. of water were added. The mixture was removed from the mixer and formed into 1/16 inch extrudates using a hydraulic ram extruder. The reaction mixture composition is set forth in Table 4, hereinafter presented. The extrudates were then placed into a polypropylene jar and put into a steam chest at 100° C to crystallize. After 72 hours the material was removed from the steam chest and a portion was washed free of excess alkali and dried. X-ray analysis of the dried portion showed it to be composed of 65 wt. % crystalline zeolite ZSM-4.

EXAMPLE 7

A preparation in the manner of Example 3, after crystallization, was thoroughly washed to remove all traces of excess alkali and unreacted soluble silicate. Fifty nine grams of the washed sample was given five 1 hour soaks at room temperature using one liter of 0.1 N NaOH in each contact. The material was then washed NaOH free and dried at 120° C. The dried sample was then given six 1 hour ion exchanges at 180°-200° F using 500 grams of 10 weight percent $NH_4Cl$ solution per 50 grams of solid sample. The sample was washed $Cl^-$ free, dried at 120° C, and calcined for 1 hour at 1000° F in 5% $O_2$ atmosphere saturated with water vapor.

The catalyst so prepared was evaluated for catalytic acticity using the low temperature toluene disproportionation test, hereinafter LTD. The activity of the catalyst, expressed as the second order reaction rate constant, was $3.1 \times 10^{-5}$ 1/mole-sec.

EXAMPLE 8

A preparation in the manner of Example 3 was modified only by the addition of 60 grams of NaCl to the sodium silicate containing solution. After crystallization, the sample was washed, dried at 120° C and ion exchanged with $NH_4Cl$ in the manner presented in Example 7.

The catalyst so prepared was evaluated by the LTD test and gave an activity of $8.2 \times 10^{-5}$ 1/mole-sec.

EXAMPLE 9

Three hundred grams of Georgia kaolin, calcined 6 hours at 1800° F in air, was dry blended with 270 grams of Hi-Sil (precipitated hydrated $SiO_2$ containing about 6 wt. % free $H_2O$ and 4.5 wt. % bound $H_2O$ of hydration and having a partical size of about 0.02μ). To this dry mixture was added a solution containing 200 grams of Q-brand sodium silicate, 9 grams of sodium hydroxide, 60 grams of sodium chloride and 370 grams of water. The resultant mixture was thoroughly blended in a muller mixer for ½ hour. The material was then extruded through 3/32 inch die plate using a California pellet mill. The extrudates were dried for 3 hours at 250° F, covered with a solution containing 76 grams of tetrapropylammonium bromide, 60 grams of sodium chloride and 525 grams of water and put in a steam chest to crystallize at 212° F. The reaction mixture had the composition set forth in Table 4, hereinafter presented. After 12 days the product was identified as 60 weight percent crystalline ZSM-5.

The crystallized product was processed into a catalytic form by washing salt free, calcining 3 hours at 700° F in air, ion exchanging with 1 N $NH_4NO_3$ solution (4 times at 180° F using approximately 4 grams of solution per gram of extrudate), drying and calcining 10 hours at 1000° F in air. The finished product was evaluated for physical strength and gave 37 lbs/inch crush strength.

EXAMPLE 10

One hundred fifty grams of Georgia kaolin, calcined 6 hours at 1800° F in air, was dry blended with 150 grams of Hi-Sil and 45 grams of Solka-Floc (finely divided wood pulp derivative which is practically ashless and, when bone dry, is at least 99.5 percent cellulose). To this mixture was added a solution containing 35 grams of Q-brand sodium silicate, 12 grams of sodium hydroxide, 38 grams of tetrapropylammonium bromide and 200 grams of water. The resultant mixture was blended in a muller mixer for ½ hour, then extruded through a 1/16 inch die plate using an hydraulic extruder. The extrudate was dried for 3 hours at 250° F; then 125 grams of the extrudate was covered with a solution containing 30 grams of sodium chloride, 19 grams of tetrapropylammonium bromide and 132 grams of water and placed in steam chest to crystallize at 212° F. The reaction mixture composition of this example is set forth in Table 4, hereinafter presented. After 9 days the product was determined by X-ray diffraction analysis to be 70 percent weight crystalline ZSM-5.

The crystallized product was processed into a catalytic form by the procedure of Example 9 and evaluated for catalytic activity. The catalytic activity was reported as 52.6 percent weight n-heptane converted and 16.1 percent weight benzene converted to alkylated aromatics.

EXAMPLE 11

Three hundred grams of Georgia kaolin, calcined 6 hours at 1800° F in air, was dry blended with 188 grams of Hi-Sil and 60 grams of Solka-Floc. To this mixture was added a solution containing 260 grams of Q-brand sodium silicate, 50 grams of tetrapropylammonium bromide, 20 grams of sodium chloride and 150 grams of water. The resultant mixture was blended in a muller mixer for an hour then extruded through a 1/16 inch die plate using a California pellet mill. The extrudate was dried for about 16 hours at 250° F in its own atmosphere. The dried extrudate was covered with a solution containing 6 grams of sodium chloride per 100 ml. of $H_2O$ and placed in a steam chest at 212° F to crystallize. The composition of the reaction mixture of this example is listed in Table 4, hereinafter presented. The amount of solution used was approximately 100 ml. of solution per 100 grams of dried extrudate. After 6 days, analysis showed the product to be 65 weight percent crystalline ZSM-5.

The crystallized product was processed into a catalytic form and evaluated for catalytic activity. The catalytic activity results were 50.2 percent weight n-heptane conversion and 16.9 percent weight benzene conversion to alkylated aromatics.

EXAMPLE 12

Four hundred sixty grams of uncalcined Georgia kaolin was dry blended with 180 grams of Hi-Sil and 30 grams of Solka-Floc. To this dry blend was added 350 ml. of water and blended for 30 minutes in a muller mixer. The mixture was then extruded through a 1/16 inch die plate using a California pellet mill, dried for about 16 hours at 230° F and then calcined 3 hours at 1800° F in air. The calcined extrudates were then covered with a solution in the ratio of 135 grams of solution per 100 grams of extrudate and placed into a steam chest at 212° F to crystallize. The solution was comprised of 30 parts tetrapropylammonium bromide, 3 parts sodium chloride, 2 parts sodium hydroxide and 100 parts water all on a weight basis. The reaction mixture composition was as listed in Table 4, hereinafter presented. After 7 days, analysis showed the product to be 55 weight percent crystalline ZSM-5. The crystallized product was processed into a catalytic form by the method of Example 9. The finished product was evaluated for physical strength and gave 56 lbs/inch crush strength.

EXAMPLE 13

Four hundred grams of Georgia kaolin and about 120 grams of $H_2O$ were mulled together for 30 minutes in a Cincinnati Muller. The mixture was extruded through 1/16 inch die plate. The extrudate was sized into $\frac{1}{4}$ inch to 1 inch length and dried at 230° F for 3 hours. The high temperature calcination was done in an open crucible using a thermolyne furnace. The temperature was raised up to 1900° F in 500° F stages and held at 1900° F for 3 hours.

EXAMPLE 14

Twenty grams of the extrudate of Example 13 was added to 30 grams of solution of the following composition:
NaOH; 80 g.
TMACl; 30 g.
$H_2O$; 400 g.
The reaction mixture had the composition listed in Table 4, hereinafter presented. It was placed in a polypropylene bottle at ambient temperature for 48 hours. It was then aged at 212° F for 48 hours. The product was 50 weight percent crystalline ZSM-4.

EXAMPLE 15

Ten thousand and eight grams of tri-n-propylamine, 16,524 grams of methyl ethyl ketone and 8,604 grams of n-propyl bromide were mixed in an autoclave for 15 minutes. One hundred and twenty three pounds of water was added to the mixture. The solution was reacted at 220° F for 15 hours in a stirred autoclave. The resulting aqueous phase is designated Solution A.

A 2340 g. portion of Georgia kaolin, Glomax HE, and 733 g. of Ludox (LS) (A colloidal dispersion of 30 wt. % $SiO_2$) were thoroughly mixed in a muller mixer for 30 minutes. The mixture was extruded through a 1/16 inch die plate on a Bonnot extruder. The extrudate was dried at 1000° F in air, for 3 hours. Thirty six grams of the dried extrudate was added to a solution of 1.05 grams NaOH pellets (97.7% wt. NaOH), 1.5 grams Q-brand sodium silicate, 5.4 grams NaCl, 157.5 grams water and 25.9 grams Solution A. The mixture was placed in a static bomb and reacted at 300° F. The composition of the mixture was as listed in Table 4, hereinafter presented. After 72 hours, X-ray diffraction analysis showed the product to be 50 wt. % crystalline ZSM-5.

EXAMPLE 16

A mixture containing 180 grams of Georgia kaolin, calcined 6 hours at 1700° F, 361.05 grams of Q-brand sodium silicate, 60 grams of NaOH, 69.4 grams of a 50 percent weight solution of tetramethylammonium chloride and 100 grams of $H_2O$ was prepared by thoroughly blending in a Waring blender. The mixture had a composition in terms of mole ratios of oxides as listed in Table 4, hereinafter presented. It was placed into a polypropylene jar and placed in a steam chest to crystallize at 100° C. After 48 hours, X-ray analysis proved the product to be 85 weight percent crystalline ZSM-4.

EXAMPLE 17

Eight hundred grams of Georgia kaolin in the raw, as received state, 200 grams Solka-Floc, and 240 grams water were mixed in a muller mixer. The mixture was extruded through a 1/25 inch die plate on a Bonnot extruder. The extrudate was dried at 250° F and then calcined at 1800° F for 6 hours in air. Thirty two and four tenths grams of 50% weight NaOH in water, 18 grams NaCl, 27.6 grams of 50% weight tetramethylammonium chloride in water, and 72 grams of water were added to 60 grams of the calcined extrudate. The mixture, having a composition as indicated in Table 4, was aged at 100° F for 24 hours with gentle agitation. After 72 hours at 210° F with no agitation, the product was analyzed to contain 55 wt. % crystalline ZSM-4.

EXAMPLE 18

Two thousand grams of Georgia kaolin were mixed in a muller mixer with 460 grams of water for 30 minutes. The mixture was extruded on a Bonnot extruder through a 1/16 inch die plate. The extrudate was dried at 250° F and then calcined at 1800° F for 3 hours in air. A crystallization solution was prepared by dissolving 80 grams of NaOH pellets, 30 grams of tetramethylammonium chloride and 51 grams of NaCl in 1148 grams of water. Three hundred fifty grams of this solution was added to each 100 grams of extrudate. The mixture, having the composition listed in Table 4, was aged at ambient temperature for 24 hours. The mixture was then transferred to a steam chest at 100° C.

After 72 hours, the mixture was removed from the steam chest, washed free of excess alkali and dried. X-ray diffraction analysis of the product revealed it to be 55 wt. % crystalline ZSM-4.

EXAMPLE 19

Two hundred thirty grams of raw Georgia kaolin, 90 grams of Hi-Sil (precipitated hydrated $SiO_2$ containing about 6 wt. % free $H_2O$ and 4.5 wt. % bound $H_2O$ of hydration) and approximately 130 grams of water were mixed in a muller mixer for 30 minutes. The mixture was extruded on a Bonnot extruder through a 1/16 inch die plate. The extrudate was dried in air overnight, then placed in a cold furnace. The extrudate was slowly heated to 1900° F in air and kept at 1900° F for 1 hour. One hundred grams of the calcined extrudate was added to a solution containing 12.5 grams of tetrapropylammonium bromide, 2.8 grams of NaOH pellets and 200 grams of water. The mixture, which had the composition listed in Table 4, was transferred into a polypropylene bottle and placed in a steam chest at 100° C. After 10 days a portion of the mixture was washed free of excess alkali and dried. X-ray diffraction analysis revealed the washed sample to be 50 wt. % crystalline ZSM-5.

EXAMPLE 20

Eighteen hundred grams of Georgia kaolin, calcined 6 hours at 1800° F in air, was dry mixed in a muller mixer with 1,458 grams Hi-Sil (finely precipitated hydrated $SiO_2$ with 6 wt. % free water and 4.5 wt. % bound $H_2O$ of hydration). To this dry mixture was added a solution containing 1,200 grams of Q-brand sodium silicate, 220 grams of NaOH pellets (98.9 wt. % NaOH), 290.5 grams of $Al_2(SO_4)_3 \cdot 14H_2O$ and 1,590 grams water. The resulting mixture was mixed for 2 hours and then extruded on a California pellet mill through a 3/32 inch die plate. The extrudate was dried at 250° F and 200 grams of extrudate was placed in a static bomb. To the bomb was added a solution of 35.4 grams tetrapropylammonium bromide in 188 grams of water. The bomb was sealed and placed in an oil bath at 350° F. The reaction mixture had a composition in mole ratio of oxides as listed in Table 4, hereinafter presented. After 40 hours, the mixture was washed free of excess alkali and dried. X-ray diffraction analysis proved the product to contain 60 wt. % crystalline ZSM-5.

EXAMPLE 21

Three hundred and four grams of Georgia kaolin, calcined 6 hours at 1700° F in air, 76 grams of Q-brand sodium silicate, 38 grams of NaOH pellets (98.7% wt. NaOH), 28 grams of Solka-Floc and 155 grams of water were mixed in a muller mixer. The mixture was extruded through a 1/16 inch die plate on a hydraulic ram extruded and dried at 120° C for 3 hours. Ninety five grams of the resulting extrudate was added to a solution containing 150 grams of Q-brand sodium silicate, 25 grams of tetrapropylammonium bromide, 10 grams of NaOH pellets (98.5% wt. NaOH) and 50 grams of water. The mixture, which had the composition listed in Table 4, was placed in a steam chest at 100° C. After 4 days, the mixture was washed free of excess alkali and dried. X-ray diffraction analysis proved the product to be devoid of any crystalline ZSM-5. It was, instead a mixture of zeolite P and zeolite S. This example is a further demonstration of the critical nature of the reaction mixture of the present improved method.

EXAMPLE 22

Five thousand grams of raw Georgia kaolin were well mixed with 4,720 grams of Ludox (LS) (colloidal dispersion of 30 wt. % $SiO_2$) and 1,000 grams of water. The mixture was dried in a Koline-Sanderson spray drier. More than 30 wt. % of the spray dried particulates were larger than 200 mesh. The particulates were calcined at 2,000° F for 6 hours in air. One hundred grams of the calcined particulates were mixed with a solution containing 18.7 grams of tetrapropylammonium bromide, 2.9 grams of NaOH pellets (97.5% wt. NaOH), 4.16 grams of Q-brand sodium silicate, 50 grams of NaCl and 500 grams of water. The resulting mixture, which had the mole ratio of oxides composition as set forth in Table 4, was transferred to a static bomb and placed in an oil bath at 300° F. After 72 hours, the product was washed of excess alkali, dried and analyzed by X-ray diffraction. The product was determined to be 50 weight percent crystalline ZSM-5.

The raw Georgia kaolin used in examples 2, 4, 12, 13, 17, 18, 19 and 22 had a water content of 8 weight percent.

TABLE 4

| Example | \multicolumn{14}{c}{REACTION MIXTURE COMPOSITIONS IN MOLE RATIOS OF OXIDES} |
|---|---|---|---|---|---|---|---|---|---|---|---|---|---|---|
| | 6 | 9 | 10 | 11 | 12 | 14 | 15 | 16 | 17 | 18 | 19 | 20 | 21 | 22 |
| $\dfrac{Na_2O+R_2O}{Al_2O_3}$ | 0.62 | 0.41 | 0.58 | 0.35 | 0.26 | 0.74 | 0.19 | 1.73 | 1.27 | 0.67 | 0.18 | 0.72 | 1.72 | 0.23 |
| $\dfrac{Na_2O+R_2O}{SiO_2}$ | 0.25 | 0.072 | 0.104 | 0.070 | 0.079 | 0.37 | 0.081 | 0.42 | 0.64 | 0.33 | 0.052 | 0.140 | 0.37 | 0.069 |
| $\dfrac{Na_2O}{Na_2O+R_2O}$ | 0.92 | 0.73 | 0.52 | 0.80 | 0.31 | 0.88 | 0.53 | 0.90 | 0.78 | 0.88 | 0.60 | 0.78 | 0.91 | 0.54 |
| $\dfrac{SiO_2}{Al_2O_3}$ | 2.48 | 5.69 | 5.57 | 5.00 | 3.30 | 2.00 | 2.43 | 4.11 | 2.00 | 2.00 | 3.51 | 5.24 | 4.66 | 3.22 |
| $\dfrac{H_2O}{R_2O+Na_2O}$ | 10.0 | 68 | 60 | 82 | 67 | 20.5 | 303 | 12.9 | 17.9 | 55.6 | 190 | 35 | 16 | 363 |
| $SiO_2$ from a non-clay source/clay | 0.13 | 1.0 | 0.97 | 0.81 | 0.35 | 0 | 0.10 | 0.57 | 0 | 0 | 0.41 | 0.96 | 0.69 | 0.31 |

LTD EXPERIMENTAL PROCEDURE

The experimental evaluations were conducted using a microreactor (15 cc max volume), reagent grade toluene (percolated through alumina). The operating procedure was to fill the complete reaction system with liquid at room temperature then raise the temperature to the operating temperature in 40 minutes or less. When the catalyst bed reached reaction temperature, this was taken as the reference to zero time. The product was continually collected over the course of the run, but only that product collected over the final five minutes of the time period specified was used for product analysis. That is to say that the product analysis reported for a sample after one hour on stream was for a sample taken for the time period 55–60 minutes.

The product analysis was performed by gas phase chromatography employing an F&M Model 5754 temperature programmed for 80° to 125° C at 4° C/min. and using helium as a carrier gas at 50 cc/min. A 24-foot chromatographic column was employed packed with 4% diisodecaphthalate, 4% bentone 34 supported on 60 to 80 mesh Chromosorb W HMDS.

RESULTS AND DISCUSSION

The kinetic model used was for the reaction:

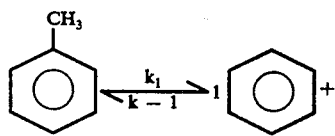

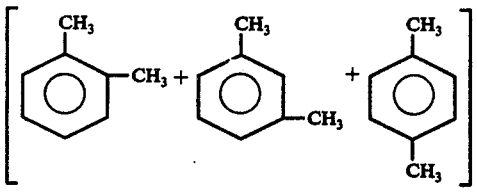

which is a second order reaction in toluene and assumes that all three xylenes behave as a single species. The integrated rate equation is readily derived or can be found in several reference texts. Employing the same equilibrium values for reactant and products reported, the following expression for the reaction rate constant, $k_1$, was obtained.

$$k_1 = \frac{1}{t}\left(.073 \ln 0.16 \left(\frac{3.62-X}{0.58-X}\right)\right)$$

where $t$ = residence time, sec.
$X$ = toluene conversion, weight %.

What is claimed is:

1. In a method for preparing a crystalline aluminosilicate zeolite from a reaction mixture containing sources of alkali metal cations, tetraalkylammonium cations, silica, alumina and water, said reaction mixture being maintained at a temperature of from about 75° C to about 205° C for from about 1 hour to about 60 days to crystallize said zeolite therefrom, the improvement wherein said zeolite is ZSM-4 or ZSM-5, characterized by a crystallinity of greater than 40 percent at the time of formation, prepared from a reaction mixture having the following compositional range in terms of mole ratios of oxides:

|  | ZSM-4 | ZSM-5 |
|---|---|---|
| $Na_2O+R_2O/Al_2O_3$ | 0.60–1.75 | 0.15–0.85 |
| $Na_2O+R_2O/SiO_2$ | 0.24–0.65 | 0.04–0.18 |
| $Na_2O/Na_2O+R_2O$ | 0.75–0.92 | 0.30–0.85 |
| $SiO_2/Al_2O_3$ | 1.8–4.3 | 1.8–6.0 |
| $H_2O/R_2O+Na_2O$ | 9–60 | 35–360 | wherein R is a tetramethylammonium cation for ZSM-4 preparation and a tetraalkylammonium cation, the alkyl groups of which contain 2-5 carbon atoms, for ZSM-5 preparation, and wherein at least about 70 weight percent of the $Al_2O_3$ is provided by an alumina-containing clay, said clay having been heated to a temperature of at least 1000° F, and further wherein the $SiO_2$ in the reaction mixture is provided such that the ratio of $SiO_2$ from a non-clay source/$SiO_2$ from said clay is from 0 to about 5.

2. In the method of claim 1, the improvement wherein the reaction mixture has the following compositional range in terms of mole ratios of oxides:

$Na_2O+R_2O/Al_2O_3$; 0.60–1.75
$Na_2O+R_2O/SiO_2$; 0.24–0.65
$Na_2O/Na_2O+R_2O$; 0.75–0.92
$SiO_2/Al_2O_3$; 1.8–4.3
$H_2O/R_2O+Na_2O$; 9–60 wherein R is a tetramethylammonium cation and wherein at least about 70 weight percent of the $Al_2O_3$ in the reaction mixture is provided by an alumina-containing clay.

3. In the method of claim 1, the improvement wherein the reaction mixture has the following compositional range in terms of mole ratios of oxides:

$Na_2O+R_2O/Al_2O_3$; 0.15–0.85
$Na_2O+R_2O/SiO_2$; 0.04–0.18
$Na_2O/Na_2O+R_2O$; 0.30–0.85
$SiO_2/Al_2O_3$; 1.8–6.0
$H_2O/R_2O+Na_2O$; 35–360 wherein R is a tetraalkylammonium cation, the alkyl groups of which contain from 2 to 5 carbon atoms, and wherein at least about 70 weight percent of the $Al_2O_3$ in the reaction mixture is provided by an alumina-containing clay.

4. In the method of claim 1, the improvement wherein at least about 80 weight percent of the $Al_2O_3$ in the reaction mixture is provided by an alumina-containing clay.

5. In the method of claim 2, the improvement wherein at least about 80 weight percent of the $Al_2O_3$ in the reaction mixture is provided by an alumina-containing clay.

6. In the method of claim 3, the improvement wherein at least about 80 weight percent of the $Al_2O_3$ in the reaction mixture is provided by an alumina-containing clay.

7. In the method of claim 1, the improvement wherein said alumina-containing clay is kaolin, halloysite or montmorillonite.

8. In the method of claim 2, the improvement wherein said alumina-containing clay is kaolin, halloysite or montmorillonite.

9. In the method of claim 3, the improvement wherein said alumina-containing clay is kaolin, halloysite or montmorillonite.

10. In the method of claim 4, the improvement wherein said alumina-containing clay is kaolin, halloysite or montmorillonite.

11. In the method of claim 5, the improvement wherein said alumina-containing clay is kaolin, halloysite or montmorillonite.

12. In the method of claim 6, the improvement wherein said alumina-containing clay is kaolin, halloysite or montmorillonite.

13. In the method of claim 7, the improvement wherein said alumina-containing clay is kaolin.

14. In the method of claim 8, the improvement wherein said alumina-containing clay is kaolin.

15. In the method of claim 9, the improvement wherein said alumina-containing clay is kaolin.

16. In the method of claim 10, the improvement wherein said alumina-containing clay is kaolin.

17. In the method of claim 11, the improvement wherein said alumina-containing clay is kaolin.

18. In the method of claim 12, the improvement wherein said alumina-containing clay is kaolin.

* * * * *

UNITED STATES PATENT AND TRADEMARK OFFICE
CERTIFICATE OF CORRECTION

PATENT NO. : 4,091,007
DATED : May 23, 1978
INVENTOR(S) : FRANCIS G. DWYER and ALBERT B. SCHWARTZ It is certified that error appears in the above-identified patent and that said Letters Patent are hereby corrected as shown below:

Column 15, line 5 " 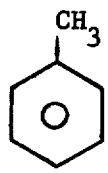 " should be -- 2 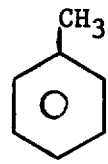 --.

Signed and Sealed this

Twelfth Day of December 1978

[SEAL]

Attest:

RUTH C. MASON
Attesting Officer

DONALD W. BANNER
Commissioner of Patents and Trademarks